United States Patent [19]
Jacobsen et al.

[11] Patent Number: 4,912,108
[45] Date of Patent: Mar. 27, 1990

[54] PYRIDOQUINOXALINE COMPOUNDS AND THEIR PREPARATION AND USE AS GLUTAMATE ANTAGONISTS

[75] Inventors: Poul Jacobsen, Rødovre; Flemming E. Nielsen, Virum; Tage Honore, Måløv, all of Denmark

[73] Assignee: A/S Ferrosan, Soborg, Denmark

[21] Appl. No.: 347,141

[22] Filed: May 3, 1989

Related U.S. Application Data

[62] Division of Ser. No. 156,539, Feb. 16, 1988.

[30] Foreign Application Priority Data

Mar. 23, 1987 [DK] Denmark .............................. 1467/87

[51] Int. Cl.$^4$ .................... A61K 31/495; C07D 487/04
[52] U.S. Cl. ..................................... 514/250; 544/345
[58] Field of Search .......................... 544/345; 514/250

[56] References Cited

U.S. PATENT DOCUMENTS 4,764,518  8/1988  Laruelle .............................. 544/345

Primary Examiner—Mark L. Berch
Attorney, Agent, or Firm—Gordon W. Hueschen

[57] ABSTRACT

Heterocyclic dihydroxyquinoxaline compounds having the formula

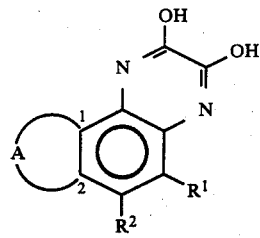

wherein —A— together with the two carbon atoms denoted as 1 and 2 is selected from

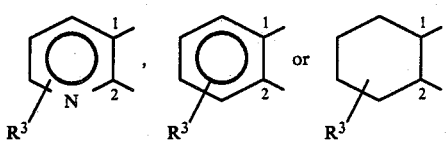

$R^1$, $R^2$ and $R^3$ are independently H, halogen, CN, $NH_2$, $NO_2$, $SO_3H$, $SO_2NH_2$, or $CONH_2$ The invention also relates to a method of preparing the compounds, pharmaceutical compositions thereof, and their use.

The compounds are useful in the treatment of indications caused by hyperactivity of the excitatory neurotransmitters.

8 Claims, No Drawings

PYRIDOQUINOXALINE COMPOUNDS AND THEIR PREPARATION AND USE AS GLUTAMATE ANTAGONISTS

This is a division of application Ser. No. 156,539, filed Feb. 16, 1988.

The present invention relates to therapeutically active heterocyclic compounds, a method of preparing the same, pharmaceutical compositions comprising the compounds, and a method of treating therewith.

The heterocyclic compounds of the invention have the general formula I

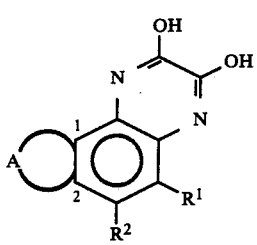

ps wherein -A- together with the two carbon atoms denoted as 1 and 2 is selected from

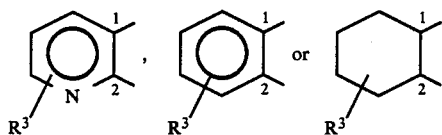

ps $R^1$, $R^2$ and $R^3$ are independently H, halogen, CN, $NH_2$, $NO_2$, $SO_3H$, $SO_2NH_2$, or $CONH_2$ The invention also relates to a method of preparing the above-mentioned compounds. This method comprises (a) reacting a compound having the formula II

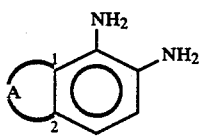

wherein -A-, 1 and 2 have the meanings defined above, with oxalate or a reactive derivative thereof to form a compound of formula I, or (b) refluxing a compound having the formula III

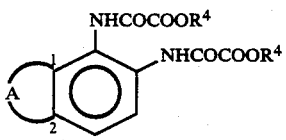

wherein -A-, 1 and 2 have the meanings defined above and $R^4$ is lower alkyl in a mineral acid, to form a compound of formula I, or (c) nitrating a compound having the formula IV

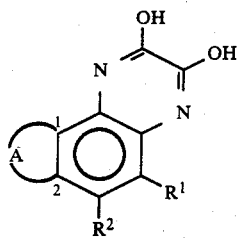

wherein -A- together with the two carbon atoms denoted as 1 and 2 is selected from

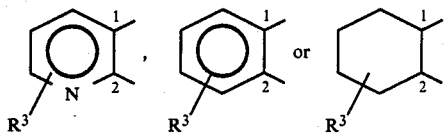

wherein at least one of $R^1$, $R^2$ and $R^3$ is hydrogen and the other are as defined above, to form a compound of formula I, or (d) reducing a compound having the formula V

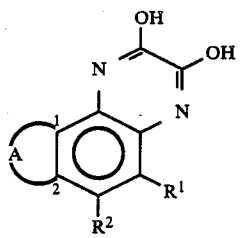

wherein -A- together with the two carbon atoms denoted as 1 and 2 is selected from

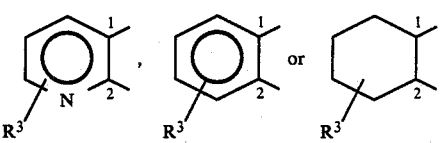

wherein at least one of $R^1$, $R^2$ and $R^3$ is nitro and the other are as defined above, to form a compound of formula I, wherein at least one of $R^1$, $R^2$ and $R^3$ is amino, or (e) reacting a compound having the formula VI

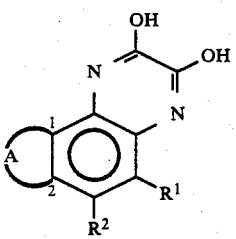

wherein -A- together with the carbon atoms denoted as 1 and 2 is selected from

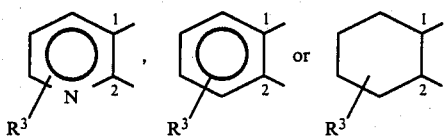

wherein at least one of $R^1$, $R^2$ and $R^3$ is $N_2^+$ and the other are as defined above, with potassium tetracyanonickelate to form a compound of formula I, wherein at least one of $R^1$, $R^2$ and $R^3$ is CN.

L-glutamic acid, L-aspartic acid and a number of other closely related amino acids have in common the ability to activate neurons in the central nervous system (CNS). Biochemical, electrophysiological and pharmacological studies have substantiated this and demonstrated that acidic amino acids are transmitters for the vast majority of excitatory neurons in the mammalian CNS.

Interaction with glutamic acid mediated neurotransmission is considered a useful approach in the treatment of neurological and psychiatric diseases. Thus, known antagonists of excitatory amino acids have shown potent antiepileptic and muscle relaxant properties (A. Jones et al., Neurosci. Lett. 45, 157–61 (1984) and L. Turski et al., Neurosci. Lett. 53, 321–6 (1985)).

It has been suggested that accumulation of extracellular excitatory and neurotoxic amino acids, followed by hyperstimulation of neurons, may explain the neuronal degenerations seen in neurological diseases as Huntingtons chorea, Parkinsonism, epilepsia, senile dementia, and deficiencies of mental and motoric performance seen after conditions of brain ischemia, anoxia and hypoglycemia (E. G. McGeer et al., Nature, 263, 517–19 (1976) and R. Simon et al., Science, 226, 850–2 (1984).

Excitatory amino acids exert their actions via specific receptors located postsynaptically or presynaptically. Such receptors are at present conveniently subdivided into three groups based on electrophysiological and neurochemical evidence: 1 the NMDA (N-methyl-D-aspartate) receptors, 2 the quisqualate receptors, and 3 the kainate receptors. L-glutamic acid and L-aspartic acid probably activate all the above types of excitatory amino acid receptors and possibly other types as well.

The consequence of excitatory amino acid interaction with postsynaptic receptors is an increase in intracellular cGMP levels (G. A. Foster et al., Life Sci. 27, 215–21 (1980)) and an opening of $Na^+$-channels (A. Luini et al., Proc. Natl. Acad. Sci. 78, 3250–54 (1981)). $Na^{30}$-influx in the neurons will depolarize the neuronal membranes, initiate an action potential and ultimately lead to a release of transmitter substance from the nerve terminal The effects of test compounds on the above mentioned secondary responses to receptor interaction can be tested in simple in vitro systems.

The above mentioned classification of excitatory amino acid receptors into NMDA, quisqualate, and kainate receptors is based primarily on the following electrophysiological and neurochemical findings.

(1) N-methyl-D-aspartate (NMDA) receptors exhibit high selectivity for the excitant NMDA. Ibotenic acid, L-homocysteic acid, D-glutamic acid and trans-2,3-piperidine dicarboxylic acid (trans- 2,3-PDA) exert a strong to moderate agonist activity on these receptors. The most potent and selective antagonists are the D-isomers of the 2-amino-5- phosphonocarboxylic acids, e.g., 2-amino-5-phosphono-valeric acid (D-APV) and 2-amino-7-phosphonoheptanoic acid (D-APH), while moderate antagonist activity is shown by the D-isomers of long chain 2-amino dicarboxylic acids (e.g.,D-2-mino-adipic acid) and long chain diaminodicarboxylic acids (e.g.,diaminopimelic acid). The NMDA-induced synaptical responses have been extensively investigated in the mammalian CNS, especially in the spinal cord (J. Davies et al., J. Physiol. 297, 621–35 (1979) and the responses have been shown to be strongly inhibited by $Mg^{2+}$.

It is well known that NMDA antagonists have anticonvulsant activity against seizures of diverse origin (Jones et al., Neurosci. Lett. 45, 157–61 (1984)), and that the potencies of the substances in seizure tests correlate well with the ability of the compounds to block NMDA responces in in vivo and in vitro electrophysiological experiments (Watkins et al., Annu. Rev. Pharmacol. Toxicol. 21, 165–204 (1981)).

NMDA antagonists are therefore useful as anticonvulsants, especially as anti-epileptics.

(2) Quisqualate receptors are activated selectively by quisqualic acid, other potent agonists being AMPA (2-amino-3-hydroxy-5-methyl-4-isoxazolepropionic acid) and L-glutamic acid. Glutamic acid diethyl ester (GDEE) is a selective but very weak antagonist of this site. Quisqualate receptors are relatively insensitive to $Mg^{2+}$.

It is well known that an excitatory aminoacid projection from prefrontal cortex to nucleus accumbens (a special part of the forebrain having dopamine neurons) exists (Christie et al.,J. Neurochem. 45, 477–82 (1985)). Further it is well known that glutamate modulates the dopaminergic transmission in the striatum (Rudolph et al., Neurochem.int. 5, 479–86 (1983)) as well as the hyperactivity connected with presynaptic stimulation of the dopamine system with AMPA in nucleus accumbens (Arnt. Life Sci. 28, 1597–1603 (1981)).

Quisqualate antagonists are therefore useful as a new type of neuroleptic.

(3) Kainate receptors. Excitatory responses to kainic acid are relatively insensitive to antagonism by NMDA-antagonists and by GDEE, and it has been proposed that kainic acid activates a third subclass of acidic amino acid receptor. Certain lactonized derivatives of kainic acid are selective antagonists (O. Goldberg et al., Neurosci. Lett. 23, 187–91 (1981)) and the dipeptide 3-glutamyl-glycine also shows some selectivity for kainate receptors. $Ca^{2+}$ but not $Mg^{2+}$ is a strong inhibitor of kainic acid binding.

The affinity of a substance for one or more of the different types of excitatory amino acid receptors may be studied in simple binding experiments. In essense, the method involves incubation of a particular selected radiolabelled ligand and the particular specific substance to be investigated with brain homogenate which contains the receptor. Measurement of receptor occupancy is made by determination of the radioactivity bound to the homogenate and subtraction of nonspecific binding.

The influence of glutamic acid analogues on secondary effects of glutamate receptor interactions, such as on c-GMP formation and on $Na^+$-efflux, may be studied in vitro by using brain slices. Such experiments will provide information as to the efficacies (agonist/antagonist) of the test substances. This is in contrast to binding studies, which only provide information on the affinities of the compounds for the receptor.

It has now been found that the heterocyclic compounds of the invention have affinity for the glutamate receptors and are antagonists in connection with these types of receptors, which makes them useful in the treatment of any of the numerous indications caused by hyperactivity of excitatory amino acids.

The quisqualate receptor binding activity of the compounds of the present invention can be illustrated by determining their capability for displacing radioactively labelled 2-amino-3hydroxy-5-methyl-4-isoxazolepropionic acid (AMPA) from the quisqualate type receptors.

The quisqualate antagonistic properties of the compounds is demonstrated by their capability to antagonize quisqualic acid stimulated Na+-efflux from rat striatal slices.

The NMDA antagonistic properties of the compounds is illustrated by determining their capability to antagonize NMDA stimulated $^3$H-GABA release from cultured mouse cortex neurons.

The displacement activity of the compounds may be shown by determining the $IC_{50}$ value which represents the concentration ($\mu$g/ml) which causes a displacement of 50% of the specific binding of $^3$H-AMPA.

The quisqualate antagonism is measured by determining the $EC_{50}$ value which represents the concentration which reduces the rate of quisqualic acid stimulated sodium efflux by 50%.

The NMDA antagonistic activity of the compounds may be shown by determining the $IC_{50}$ value, which represents the concentration ($\mu$g/ml) which inhibits 50% of NMDA induced $^3$H-GABA release. cl $^3$H-AMPA binding(Test 1)

500 $\mu$l of thawed rat cerebral cortical membrane homogenate in Tris-HCl (30 mM), CaCl$_2$ (2.5 mM) and KSCN (100 mM) pH 7.1 were incubated at 0 °0 C. for 30 min. with 25 $\mu$l $^3$H-AMPA (5 nM final concentration) and the test compound and buffer. Nonspecific binding was determined by incubation with L-glutamic acid (600 $\mu$M final concentration). The binding reaction was terminated by adding 5 ml of ice-cold buffer followed by filtration through Whatman GF/C glass fibre filters and 2×5 ml wash with ice-cold buffer. Bound radioactivity was measured by scintillation counting. $IC_{50}$ was determined by Hill analysis of at least four concentrations of test compound.

Antagonism of quisqualic acid induced $^{22}$Na+-release(Test 2)

Slices from rat striatum were preincubated with $^{22}$Na+ for 30 min. After the $^{22}$Na+loading period, the slices were successively and every minute transferred through a series of tubes, each containing 1.5 ml of a non-radioactive physiological solution saturated with O$_2$, with the help of a basket shaped sieve. Quisqualic acid (2 $\mu$g/ml) was present in the last 5 tubes and the compound to be tested was present in the same 5 tubes plus 3 tubes before. The amount of radioactivity in each washout tube as well as that left in the slices at the end of the experiment was measured by scintillation counting. $EC_{50}$-values were calculated by Hill analysis from at least three different concentrations of test compound as the concentration of test compound which reduces the efflux rate of $^{22}$Na+-ions to 50% of the efflux rate in the absence of test compound.

Inhibition of NMDA stimulated $^3$H-GABA release from cultured mouse cerebral cortex interneurons(Test 3)

Release experiments are performed using the model described by Drejer et al. (Life Sci. 38, 2077 (1986)). To cerebral cortex interneurons cultured in petri dishes (30mm) are added 100$\mu$g/ml 3-vinyl-GABA one hour before the experiment in order to inhibit degradation of GABA in the neurons. 30 min before the experiment 5 $\mu$Ci $^3$H-GABA is added to each culture and after this preloading period the cells are washed twice with a HEPES (N- 2 Hydroxyethylpiperazine-N'-2-ethanesulfonic acid) buffered saline (HBS) containing 10 mM HEPES, 135 mM NaCl, 5 mM KCl, 0.6 mM MgSO$_4$, 1.0 mM CaCl$_2$ and 6 mM D-glucose; pH 7 and placed in a superfusion system. This system consists of a peristaltic pump continuously delivering thermostated 37 °0 C. superfusion medium from a reservoir to the top of a slightly-tilted petri dish . The cell monolayer at the bottom of the dish is covered with a piece of nylon mesh to facilitate dispersion of medium over the cell layer. The medium is continuously collected from the lower part of the dish and delivered to a fraction collector. Initially, the cells are superfused with HBS for 15 min (flow rate 2 ml/min). Then cells are stimulated for 30 sec every 4 min by changing the superfusion medium from HBS to a corresponding medium containing NMDA and antagonists according to the following scheme:

stimulation no. 1: 3 $\mu$g/ml NMDA stimulation no. 2: 3 $\mu$g/ml NMDA+0.3 $\mu$g/ml antagonist stimulation no. 3: 3 $\mu$g/ml NMDA+3 $\mu$g/ml antagonist Test substances are dissolved in water or 48% ethanol. The final ethanol concentration in the assay must not exceed 0.1%.

The release of $^3$H-GABA in the presence of NMDA (stimulated relase in cpm) are corrected for the mean basal release (cpm) before and after the stimulation.

The stimulated release in the presence of antagonists are expressed relative to the stimulated release by NMDA alone and the $IC_{50}$ value for the antagonist is calculated (the concentration ($\mu$g/ml) of the test substance which inhibits 50% of the NMDA induced $^3$H-GABA release) either from a dose response curve or from the formula:

$$IC_{50} = \text{(applied test substance concentration)} \times \frac{1}{\left(\dfrac{C_0}{C_x} - 1\right)} \mu g/ml$$

where $C_o$ is stimulated release in control assays and $C_x$ is the stimulated release in the test assay (the calculation assumes normal mass-action interaction). 25–75% inhibition of the NMDA stimulation must be obtained, before calculation of $IC_{50}$.

Test results obtained by testing some compounds employed in the present invention will appear from the following table 1.

TABLE 1

Structure: quinoxaline-2,3-diol with fused ring A, substituents R¹, R² on the benzene ring; R³ on ring A.

| —A— | R¹ | R² | R³ | Test 1 IC$_{50}$ μg/ml | Test 2 EC$_{50}$ μg/ml | Test 3 IC$_{50}$ μg/ml |
|---|---|---|---|---|---|---|
| benzene (R³ at 1/2) | H | NO$_2$ | H | 0.69 | 14 | 0.39 |
| benzene (R³ at 1/2) | H | NH$_2$ | H | 1.1 | 23 | |
| benzene (R³ at 1/2) | H | NO$_2$ | 7-NO$_2$ | 0.06 | 2.8 | 0.3 |
| benzene (R³ at 1/2) | H | NO$_2$ | 10-NO$_2$ | 0.85 | | 0.97 |
| cyclohexane (R³ at 1/2) | H | NO$_2$ | H | 0.17 | | 0.092 |
| benzene (R³ at 1/2) | H | Br | 10-NO$_2$ | 9.2 | | 0.25 |
| pyridine (N, R³ at 1/2) | H | NO$_2$ | H | 0.61 | | 1.5 |

The invention will now be described in further detail with reference to the following examples.

EXAMPLE 1

2,3-Dihydroxy-6-nitropyrido(2,3-f)quinoxaline

A solution of 500 mg (2,35 mmol) 2,3-dihydroxypyrido(2,3-f)quinoxaline in 25 ml sulfuric acid (95–97%) was ice-cooled, and 238 mg (2,35 mmol) potassium nitrate was added. Stirring was continued at 0° C. for ½ h and then at 25° C. for 4 h. The reaction mixture was poured into 100 ml ice-water. The precipitate was filtered off and washed with water. The crude product was recrystallized (dimethyl formamide - water) to give 425 mg (70%) of pure 2,3-dihydroxy-6-nitropyrido-(2,3-f)quinoxaline, m.p. >300° C. $^1$H NMR (DMSO-d$_6$): 13,7 (2H,broad s), 9,0 (1H,d), 8,8 (1H,d), 7,86 (1H,s), 7,6 (1H, double d).

EXAMPLE 2

7-Bromo-2,3-dihydroxybenzo(f)quinoxaline

A mixture of 1,0 g (4,2 mmol) 1,2-diamino-5-bromonaphthalene and 1,2 g ( 9,5 mmol) oxalic acid dihydrate in 20 ml 4 N hydrochloric acid was refluxed for 2,5 h. After cooling to 25° C., the precipitate was filtered off and washed with water. The crude product was dissolved in 200 ml 2 N sodium hydroxide, and reprecipitated with 4N hydrochloric acid (to pH 1-2) to give 820 mg ( 67%) of pure 7-bromo-2,3-dihydroxybenzo(f)quinoxaline, m.p. >300° C. $^1$H NMR (DMSO-$d_6$): 8,6 (1H,d), 7,8 (1H,d), 7,7 (1H,d), 7,4 (1H,d), 7,3 (1H,d).

EXAMPLE 3 a. 1,2-Diethoxalylamino-4-bromonaphthalene

A solution of 10,0 g ( 37,5 mmol) 1-amino-4-bromo-2-nitronaphthalene in 700 ml ethyl acetate was hydrogenated at atm. pressure by using Ra-Ni (10 g) as a catalyst. After hydrogen uptake had ceased, the catalyst was filtered off. The filtrate was added 20 ml ( 154 mmol) triethylamine and then dropwise a solution of 15 ml ( 135 mmol) ethyl oxalyl chloride in 50 ml tetrahydrofuran. Stirring was continued at 25° C. for 1 h and then at 100° C. for 15 min. The reaction mixture was filtered and evaporated to give an oil The crude product was stirred with ethanol to give 13,1 g ( 73 %) 1,2 -diethoxalylamino- 4 -bromonaphthalene as white crystals, m.p. 164.5° C. $^1$H NMR (DMSO-$d_6$): 10,7 (1H,s), 10,3 (1H,s), 8,2 ( 1 H,s), 8,2 - 7,3 ( 4 H,m), 4,3 ( 4 H, double q), 1,4 ( 6H, double t).

b. 6-Bromo-2,3-dihydroxybenzo(f)quinoxaline

A mixture of 2,0 g (4,6 mmol) 1,2-diethoxalylamino-4-bromonaphthalene in 50 ml 2N hydrochloric acid and 25 ml acetic acid was refluxed for 1,5 h. After cooling to 25° C., the precipitate was filtered off. The crude product was recrystallized (dimethylformamide-water) to give 1,2 g ( 90%) of pure 6-bromo-2,3-dihydroxybenzo(f)quinoxaline, m.p. > 300° C. $^1$H NMR (DMSO-$d_6$): 8,8 (1H,m), 8,3 (1H,m), 7,87 (1H,s), 7,7 (2H,m).

EXAMPLE 4

2,3-Dihydroxy-benzo(f)quinoxaline-7-sulphonic acid

A mixture of 0,5 g (2,1 mmol) 1,2-diaminonaphthalene-5-sulphonic acid and 0,75 g (5,8 mmol) oxalic acid dihydrate in 25 ml 4N hydrochloric acid was refluxed for 4 h. After cooling to 25° C., the precipitate was filtered off and washed with 5 ml 4N hydrochloric acid and 5 ml ice-cooled water. The crude product was dissolved in 15 ml 4N sodium hydroxide, and then reprecipitated with 4N hydrochlorid acid to give 0,35 g ( 57%) of 2,3-dihydroxy-benzo(f)quinoxaline-7-sulphonic acid, m.p. > 300° C. IR (KBr): 3450 (m), 1690 (s), 1190 (s), 1055 (s), 1020 (s) cm$^{-1}$. $^1$H NMR (DMSO-$d_6$): 12,2 (2H,s), 8,7 (1H,d), 8,6 (1H,d), 8,0 (1H,d), 7,5 (1H,t), 7,4 (1H,d).

EXAMPLE 5

6-bromo-2,3-dihydroxy-9-nitrobenzo(f)quinoxaline and 6-bromo-2,3-dihydroxy-10-nitrobenzo(f)quinoxaline A solution of 3 g (10,3 mmol) 6-bromo-2,3-dihydroxybenzo(f)quinoxaline in 50 ml sulfuric acid (96-98%) was ice-cooled and added 1,1 g (10,9 mmol) potassium nitrate. Stirring was continued at 0° C. for 30 min. and then at 25° C. for 3 h. The reaction mixture was poured into 300 ml ice-water to give ca. 3 g of a crude product. Recrystallization (dimethylformamide-methanol) gave 1,65 g of compound A. The mother liqouer was added water to give 1,2 g of a precipitate (compound B). Compound A was recrystallized (dimethylformamide-methanol) to give 1,5 g ( 43%) of pure 6-bromo-2,3-dihydroxy-9-nitrobenzo(f)quinoxaline, m.p. > 300° C. $^1$H NMR (DMSO-$d_6$): 12,0 (2H,s), 8,5 (1H,s), 8,4 (1H,d), 8,0 (1H, double d), 5,3 (1H,s). Compound B was recrystallized (dimethylformamide-water) to give 0,8 g ( 24%) of pure 6-bromo-2,3-dihydroxy-10-nitrobenzo(f)quinoxaline, m.p. > 300° C. $^1$H NMR (DMSO-$d_6$): 12,6 (1H, broad s), 12,2 (1H, broad s), 8,3 (1H,t), 7,9 (1H,d), 7,8 (1H,s), 7,6 (1H,d).

EXAMPLE 6

2,3-Dihydroxy-6,7-dinitrobenzo(f)quinoxaline 2,3-Dihydroxybenzo(f)quinoxaline (1.1 g, 5 mmol) was dissolved in 25 ml of conc. sulfuric acid. Then powered potassium nitrate (1.0 g, 10 mmol) was added during 5 min with stirring on an ice bath. The mixture was stirred over night at room temperature and was then poured into 100 ml of ice/water. The precipitate was isolated, washed with water, and dried. The crude mixture (consisting of the 6,7- and 6,10-dinitroisomers) was boiled with 100 ml of acetic and filtered while hot. This procedure was repeated with 50 ml of acetic acid. The almost pure product (0.56 g) was now dissolved in 15 ml of 2N sodium hydroxide, filtered and reprecipitated with 4M hydrochloric acid to give 0.47 g (30%) of the pure title compound, m.p. > 300° C., IR (KBr): 1710 cm$^{-1}$. $^1$H-NMR (DMSO-$d_6$): 7.83(t,J=8Hz,1H, H-9), 8.26 (s,1H,H-5), 8.33(d,J=8Hz, 1H,H-10), 9.03 (d,J=8Hz, H-8), 12.3 (broad s, 1H,0H),, 12.5 (broad s, 1H, OH).

EXAMPLE 7 a. 1,2-Diethoxalylaminonaphthalene 1,2-Diaminonaphthalene (9.5 g, 0.06 mol) was dissolved in 100 ml of dry tetrahydrofuran. Dry triethylamine (16.7 ml, 0.12 mol) was added and then a solution of ethyl oxalyl chloride (13.4 ml, 0.12 mol) in 50 ml of dry tetrahydrofuran was added during 30 min with stirring at 0° C. After 1 h at 0° C. the mixture was refluxed for 1 h. Then it was cooled in an ice bath, and triethylamine hydrochloride was filtered off and washed with dry tetrahydrofuran. The combined organic filtrate was now evaporated to dryness and the residue slowly crystallized. The crude product was triturated with water, filtered off and washed with ether to give 20.0 g (93%) of almost pure product, m.p. 149.7-151.1° C. Recrystallization from ethylacetate/ligroin (80-1OO° C.) afforded 16.7 g (78%) of pure product, m.p. 149.9-152.0° C., $^1$H-NMR (CDCl$_3$): 1.35 (t,J=7Hz,3H,CH$_3$),1.38(t,J=7Hz,3H,CH$_3$), 4.28(q,J=7Hz,2H,CH$_2$), 4.37(q,J=7Hz,2H,CH$_2$), 7.17–7.93(m,6H,ArH), 9.27(broad s, 1H,NH), 9.45(broad s, 1H,NH).

b. 1,2-Diethoxalylamino-4-nitronaphthalene

A solution of 1,2-diethoxalylaminonaphthalene (10.8 g, 0.03 mol) in 150 ml of acetic acid was treated dropwise with nitric acid (1.24 ml, 0.03 mol, d 1.52) and stirred over night at room temperature. Then an additional amount of nitric acid (2.0 ml, d 1.52) was added dropwise and the mixture was stirred for 17 h at room temperature. The mixture was poured into 200 ml of ice/water and the resulting precipitate was isolated by filtration and washed with water, a small amount of cold ethanol and ether affording 3.3 g (27%) of pure product, m.p. 183.0–184.0° C.

c. 2,3-Dihydroxy-6-nitrobenzo(f)quinoxaline

A suspension of 1,2-diethoxalylamino-4-nitronapthalene (3.0 g, 7.4 mmol) in 100 ml of 4M hydrochloric acid was refluxed with stirring for 3 h. The mixture was cooled, and the product was isolated by filtration and washed wi water, ethanol and ether. Yield 1.8 g (94%), m.p. >300° C., IR (KBr): 1710 cm$^{-1}$, $^1$H-NMR (DMSO-d$_6$): 7.47–7.83 (m, 2H, ArH), 8.21 (s, 1H,H-5), 8.33–8.73 (m, 2H, ArH), 12.25 (s, 1H,OH), 12,40 (s,1H,OH).

EXAMPLE 8

6-Amino-2,3-dihydroxybenzo(f)quinoxaline

A solution of stannous chloride dihydrate (3.7 g, 16 mmol) in 10 ml of conc. hydrochloric acid was added dropwise to a stirred suspension of 2,3-dihydroxy-6-nitrobenzo(f)quinoxaline (1.3 g, 5 mmol) in 8 ml of conc. hydrochloric acid. Then the mixture was stirred at 60–70° C. on an oil bath for 2 h. After cooling on ice, the precipitate was collected, dissolved in boiling water (1 l), filtered while hot, and neutralized to pH 6 with solid sodium hydrogen carbonate. The yellow product was isolated and recrystallized from DMF/water, washed with water, ethanol and ether and finally dried at 110 ° C. to give 0.90 g (63%) of pure title compound, m.p. >300° C., IR (KBr): 1690, ? 1640 and 1605 cm$^{-1}$, $^1$H-NMR (DMSO–d$_6$): 5.8 (broad s, 2H,NH2), 6.63(s,1H, H-5), 7.2-8.7 (m, 4H, ArH), 11.8 (broad s, 2H, 2OH).

EXAMPLE 9

6-Cyano-2,3-dihydroxybenzo(f)quinoxaline

6-Amino-2,3-dihydroxybenzo(f)quinoxaline (0.23 g, 1 mmol) was dissolved in 1 ml of conc. sulfuric acid, and 10 ml of water was added dropwise at 0° C. At this temperature he resulting suspension was diazotised with sodium nitrite (90 mg, 1.3 mmol) in 2 ml of water. After stirring at 0° C. for 30 min the diazo-suspension was adjusted to pH 7 with sodium hydrogen carbonate, and a solution of potassium tetracyanonickelate (0.65 g) in 10 ml of water was added in one portion. Stirring was continued for 1 h at 0° C., and then the mixture was heated on a steam-bath for 30 min. After cooling on ice, the mixture was adjusted to pH 5, and the solid was collect ed and washed with water and ethanol. Recrystallization from DMF/water with decolourising carbon followed by drying at 110° C. afforded 80 mg (34%) of pure title compound, m.p. > 300° C., IR (KBr): 2220 (CN), 1700 (C=O) and 1635 cm$^{-1}$, $^1$H-NMR (DMSO-d$_6$): 7.3-8.7 (m.5H,ArH), 12.2(broad s, 2H, 2OH).

EXAMPLE 10 a. 1,2-Diethoxalylamino-8-nitronaphthalene

A partial suspension of 1 2-diethoxalylaminonaphthalene (1,79 g, 5 mmol) in 7 ml of acetic acid and 7 ml of acetic anhydride was treated dropwise with a solution of nitric acid (1.8 ml, 43 mmol, d 1.52) in 7 ml of acetic acid, with stirring at 0° C. The resulting solution was stirred at 0° C. for 1½ h and then poured on 150 ml of ice/water. The yellow precipitate was isolated, dried and recrystallized from ethanol with decolouring carbon giving 0.67 g (33%) of the required compound, m.p. 173–175° C., $^1$H-NMR (CDCl$_3$+DMSO-d$_6$), 1,43 (t,J=7 Hz, 6H,2 CH$_3$), 4.40 (q,J=7Hz, 2H, CH$_2$), 4.42 (q,J=7Hz, 2H, CH$_2$), 7.3–8.4 (m, 5H, ArH).

b. 2,3-Dihydroxy-10-nitrobenzo(f)quinoxaline

A suspension of 1,2-diethoxalylamino-8-nitro-naphthalene (0.40 g, 1 mmol) in 20 ml of 4M hydrochloric acid was refluxed with stirring for 2 ½ h. The mixture was cooled, and the product was filtered off, washed with water, and dried to give 0.23 g (88%) of the title compound, m.p. > 300° C., IR (KBr): 1700 (C=O), 1635 cm$^{-1}$, $^1$H-NMR (DMSO-d$_6$): 7.45–8.40 (m,5H,ArH), ca. 10.5–13.0 (broad s, 1H, OH), 12.5 (broad s, 1H, OH).

EXAMPLE 11

2,3-Dihydroxy-6,10-dinitrobenzo(f)quinoxaline

Finely powdered potassium nitrate (81 mg, 0.8 mmol) was added during a few minutes to a stirred solution of 2,3-dihydroxy-10-nitrobenzo(f)quinoxaline (0.21 g, 0.B mmol) in 3 ml of conc. sulfuric acid at 0° C. After stirring over night at room temperature, the solution was poured into 50 ml of ice/water. The yellow precipitate was isolated, washed with water, dried and recrystallized from 96% ethanol affording 0.12 g (50%) of the dinitro compound, m.p.> 300° C., IR (KBr): 700 cm$^{-1}$ (C=O), $^1$H-NMR (DMSO-d$_6$): 7.72 (t,J=8 Hz,1H,H-8), 8.10 (dd,J$_{7-8}$=8Hz,J$_{7-91}$ Hz, 1H, H-7), 8.23 (s,1H,H-5), 8.55 (dd,J$_{9-8}$=8 Hz, J$_{9-7}$=1Hz, 1H,H-9), 12.9 (broad s, 1H, OH, only one exchangeable proton could be seen).

EXAMPLE 12 a. 2-Ethoxalylamino-1-nitronaphthalene

1-Nitro-2-naphthylamine (18.8 g, 0.1 mol) and dry triethylamine (14.0 ml, 0.1 mol) were dissolved in 100 ml of dry tetrahydrofuran. A solution of ethyl oxalyl chloride (11.2 ml, 0.1 mol) in 50 ml of dry tetrahydrofuran was added dropwise with stirring at 0° C. Stirring was continued at room temperature for 2 h, and then at reflux temperature for 1 ½ h. Now the mixture consisted of unreacted amine and the diacylated product. Therefore, a further equivalent of ethyl oxalyl chloride (11.2 ml, 0.1 mol) in 25 ml of dry tetrahydrofuran, and dry triethylaming (14.0 ml, 0.1 mol) was added dropwise at 0° C., and the mixture was refluxed for 3 h. After cooling on ice, triethylamine hydrochloride was removed by filtration, and the filtrate was evaporated to dryness. The residue, which crystallized by trituration with 100 ml of ether, gave 31.6 g of crude diacylated product. However, crystallization from ca 400 ml of ethanol afforded 21.6 g (75%) of the pure monoacylated product, m.p. 139.3–139.6° C., $^1$H-NMR (CDCl$_3$): 1.42(t,J=7 Hz,3H,CH ), 4.37 (q,J=7 Hz,2H,CH$_2$), 7.2–8.4 (m,6H,ArH), 10.47 (broad s, 1H,NH).

b. 2-Ethoxalylamino-1.8-dinitronaphthalene

2-Ethoxalylamino-1-nitronaphthalene (11.5 g, 0.04 mol) was dissolved in 80 ml of sulfuric acid (d 1.84)by portionwise addition, with vigorous stirring on an ice-bath. Nitric acid (1.66 ml, 0.04 mol, d 1.52) in 20 ml of sulfuric acid (d 1.84) was added dropwise during 1 h at 0° C., and the mixture was stirred at this temperature for a further hour. The mixture was cautiously poured into 600 ml of ice/water with vigorous stirring. The yellow solid was collected, washed with water, and boiled with 300 ml of ethanol. The hot suspension was filtered and the undissolved residue was washed with 200 ml of ether to yield 7.35 g (55%) of the title compound, m.p. 232.7–233.4° C. (acetic acid),1H-NMR (DMSO-d$_6$) 1.33 (t,J=7Hz,3H,CH$_3$), 4.34 (q,J=7Hz,2H,CH$_2$), 7.7–8.6 (m,5H,ArH), 11.12 (s,1H,NH).

c. 10-Amino-2,3-dihydroxybenzo(f)quinoxaline

A solution of 2-ethoxalylamino-1,8-dinitronaphthalene (3.33 g, 0.01 mol) in 100 ml of N,N-dimethylformamide was hydrogenated at atmospheric pressure in the presence of 1 g of 5% palladium-on-charcoal for 1 ½ h. The catalyst was filtered off, washed with a small amount of N,N-dimethylformamide, and the combined filtrate was evaporated to dryness. The residue was triturated with 100 ml of ethanol, and the solid was collected and dried at 100° C. for 5 h affording 1.83 g (81%) of almost pure amino compound, m.p.>300° C., IR (KBr): 1685 cm$^{-1}$,(C=O),1H-NMR (DMSO-d$_6$): 6.9–8.3 (m,8H,ArH +NH$_2$+OH), 12.2 (broad s, 1H,OH).

EXAMPLE 13

10-Cyano-2,3-dihydroxybenzo(f)quinoxaline

10-Amino-2,3-dihydroxybenzo(f)quinoxaline (0.46 g,2 mmol) was dissolved in 2 ml of conc. sulfuric acid and 10 ml of water was added dropwise at 0° C. At this temperature the resulting suspension was diazotised with sodium nitrite (0.15 g, 2.1 mmol) in 4 ml of water. After stirring at 0° C. for 20 min a solution of potassium tetracyanonickelate (1.3 g) and sodium hydrogen carbonate (3 g) in 30 ml of water was added dropwise during 10 min pH was adjusted to about 7 with 50 ml of saturated aqueous sodium hydrogen carbonate, and the mixture was stirred at 100° C. for 1 h, and left over night at room temperature. The dark precipitate was isolated, and extracted with hot ethanol (4×50 ml). The combined extracts were evaporated to about 20 ml, and 60 mg (13%) of the cyano compound was isolated by filtration, m.p. > 300° C., IR (KBr): 2210 (CN), 1700 (C=O) cm$^{-1}$.

EXAMPLE 14

7,8,9,10-Tetrahydro-2,3-dihydroxybenzo(f)quinoxaline

A suspension of 5,6-diamino-1 2 3,4-tetrahydronaphthalene (0.32 g, 2 mmol) in 5 ml of M hydrochloric acid was refluxed with oxalic acid dihydrate (0.38, 3 mmol) for 5 h. After cooling, the precipitate was isolated by filtration, washed with water, ethanol and ether giving 0.31 g (72%) of the title compound; m.p. >300° C.; IR (KBr): 1695 cm$^{-1}$(C=O),1H-NMR (DMSO-d$_6$): 1.5–1.9 (m, 4H,2×CH$_2$), 2.5–2.8 (m,4H,2×CH$_2$), 6.63 (d,J=8Hz, 1H, ArH), 6.83 (d,J=8Hz, 1H, ArH), 10.94 (broad s, 1H, OH), 11.77 (broad s, 1H, OH)

EXAMPLE 15

7,8,9,10-Tetrahydro-2,3-dihydroxy-6-nitrobenzo(f)quinoxaline 7,8,9,10-Tetrahydro-2,3-dihydroxybenzo (f) quinoxaline (0.43 g, 2 mmol) was dissolved in 5 ml of nitric acid (d 1.48) by portionwise addition, with vigorous stirring on a salt/ice − bath at −10° C. After stirring at this temperature for 2 min, the mixture was poured onto 50 ml of ice/water. The precipitate was filtered off, washed with water, a small amount of ethanol, and ether affording 0.48 g (92%) of the mononitro compound; m.p. >300° C.; IR (KBr): 1720cm$^{-1}$, (C=O); 1H-NMR (DMSO-d$_6$): 1.5–1.9 (m, 4H, 2×CH$_2$), 2.5 - 3.0 (m, 4H, 2×CH$_2$), 7.50 (s, 1H, H-5), 11.2 (broad s, 1H, OH), 11.9 (broad s, 1H, OH).

EXAMPLE 16

6-Amino-7,8,9,10-tetrahydro-2,3-dihydroxybenzo(f)quinoxaline

A solution of 7,8,9,10-tetrahydro-2,3-dihydroxy-6-nitrobenzo(f)quinoxaline (1.5 g, 5.7 mmol) in 50 ml of N,N-dimethylformamide was hydrogenated at atmospheric pressure and room temperature in the presence of 5% palladium-on-charcoal. The catalyst was filtered off, and the filtrate was evaporated to dryness. The residue was triturated with water, the solid was collected and washed with water, and ethanol affording 1.2 g (90%) of the amino compound; m.p. > 300° C.; 1H-NMR (DMSO-d$_6$): 1.7–2.0 (m,4H,2×CH$_2$), 2.5–2.8 (m,4H, 2 × CH$_2$), 4.97 (broad s, 2H, NH$_2$), 6.53 (s, 1H, H-5), 10.5 (broad s, 1H, OH), 11.4 (broad s, 1H, OH).

EXAMPLE 17

6-Cyano-7,8,9,10-tetrahydro-2,3-dihydroxybenzo(f)quinoxaline

6-Amino-7,8,9,10-tetrahydro-2,3-dihydroxybenzo-(f)quinoxaline (0.5 g, 2.2 mmol) was dissolved in 2-3 ml of conc. sulfuric acid, and 10 ml of water was added dropwise at 0° C. At this temperature the resulting suspension was diazotised with sodium nitrite (0.18 g, 2.6 mmol) in 4 ml of water. After stirring at 0° C. for 30 min, the diazo-suspension was adjusted to pH7 with solid sodium hydrogen carbonate, and a solution of potassium tetracyanonickelate (1.3 g) in 20 ml of water was added in one portion. Stirring was continued for 1 h at 0° C., and then the mixture was heated on a steam-bath for 1 h. After cooling on ice, the mixture was adjusted to pH 5–6, and the solid was isolated and washed with water. Extraction of the solid with hot ethanol afforded 0.14 g (27%) of the required cyano compound; m.p. > 300° C., IR(KBr): 2220 (CN), 1700 cm$^{-1}$ (C=O); H-NMR (DMSO-d$_6$)= 1.6–1.9 (m, 4H, 2×CH$_2$), 2.6–2.9 (m, 4H,2 × C.H$_2$), 7.18 (s, 1H, H–5), ca 11.4 (broad s, 2H, 2×OH).

EXAMPLE 18

7,8,9,10-Tetrahydro-2,3-dihydro-5,6-dinitrobenzo(f)quinoxaline 7,8,9,10-Tetrahydro-2,3-dihydroxybenzo(f)quinoxaline (1.0 g, 4.6 mmol) was dissolved in 10 ml of nitric acid (d 1.48) by portionwise addition, with vigorous stirring in an ice-bath at 0° C. After 3 hours stirring at 0° C., the mixture was poured onto 200 ml of ice/water and stirred for a further hour. The precipitate was filtered off, washed with water, a small amount of ethanol and ether, and dried giving 1.34 g (95%) of the pure dinitro compound. The compound decomposes gradually above 275° C.;1H-NMR (DMSO-d$_6$) 1.5–2.0 (m, 4H, 2x CH$_2$), 2.4–2.9 (m, 4H, 2 ×CH$_2$), 11.5 (broad s, 2H, 2 ×OH).

EXAMPLE 19 a. 7-Cyano-1,2,3,4-tetrahydro-5,6-dinitronaphthalene

Solid sodium nitrite (0.15 g, 2.2 mmol) was added to 1.6 ml of conc. sulfuric acid with stirring at room temperature. The temperature was raised to 70° C. for about 10 min, and the resulting solution was cooled to 0° C. with an ice-bath. A solution of 7-amino-1,2,,4-tetrahydro-5,6-dinitronaphthalene (0.47 g, 2 mmol) in 5 ml of hot glacial acetic acid was added dropwise, with stirring, keeping the temperature below 40° C. Then the solution was stirred at 0° C. for 30 min, and a solution of potassium tetracyanonickelate (1.2 g) in 100 ml of saturated sodium hydrogen carbonate was added in portions with vigorous effervescence. After stirring for 1 h at room temperature, the mixture was filtered and the precipitate was washed with water, and dried. Extraction of the crude product in a Soxhlet apparatus with ligroin (100–140° C.) afforded 0.18 g (37%) of the title compound; IR(KBr): 2240 cm$_{-1}$ (CN)

b. 5-Carbamoyl-7,8,9,10-tetrahydro-2,3-dihydroxybenzo(f)quinoxaline

A solution of 7-cyano-1,2,3,4-tetrahydro-5,6-dinitronaphthalene (0.18 g, 0.73 mmol) in ethanol was hydrogenated at room temperature and atmospheric pressure in the presence of 100 mg of 5% palladium-on-charcoal. The catalyst was filtered off, and the filtrate was evaporated to dryness. The solid residue was suspended in 10 ml of 1M hydrochloric acid, oxalic acid dihydrate (0.15 g, 1.2 mmol) was added, and the mixture was refluxed for 3 h. After cooling, the solid was collected and washed with water, ethanol and ether affording 80mg (42%) of the amide; m.p. > 300° C., IR(KBr):3360, 3220, 1690, 1650, 1620 cm$^{-1}$; MS: m/e (relative intensity) 259 (M+,82), 242 (44), 231 (26), 214 (100).

EXAMPLE 20

2,3-Dihydroxy-6-sulphamoyl-benzo(f)quinoxaline

A mixture of 1.0 g (3.4 mmol) 1,2-diamino-4-sulphamoyl-naphtalene and 1.0 (7.9mmol) oxalic acid dihydrate in 20 ml 2N HCl was refluxed for 2 hours. After cooling to room temperature the precipitate was filtered off and washed with water. The crude product was recrystallized from dimethylformamide/water to give 0.6g(50%) of the title compound, M.p. > 300° C., H NMR (DMSO-d$_6$): 1.22(2H,s), 8.7(2H,m), 8.2(1H,s), 7.7-(4H,m).

EXAMPLE 21 a. 1-Amino-5-cyano-2-nitronaphtalene

To a solution of 1,6 g (5,9 mmol) 1-amino-5-bromo-2-nitronaphthalene in 50 ml dimethylformamide was added 1,1 g (11,8 mmol) cuprous cyanide. The reaction mixture was refluxed for 5 h, and then poured into a solution of 2,5 ml ethylenediamine in 80 ml water. Stirring was continued for 15 min., and then the precipitate was filtered off and washed with water and boiling ethyl acetate to give 1,0 g (80%) 1-amino-5-cyano-2-nitronaphthalene, m.p. 260–262° C. IR (KBr): 2200 cm$^{-1}$ (nitrile function).

b. 1,2-Diamino-5-cyanonaphthalene

A solution of 0,7 g (3,3 mmol) 1-amino-5-cyano-2-nitronaphthalene in a mixture of 75 ml ethanol and 75 ml ethyl acetate was hydrogenated at atm. pressure by using ca. 1 g Ra-Ni as a catalyst. The reaction mixture was filtered and evaporated in vacuo to give 1,2-diamino-5-cyanonaphthalene as yellow crystals. IR (KBr): 2220 cm$^{-1}$ (nitrile function).

c. 2,3-Dihydroxy-7-cyano-benzo[f]quinoxaline

A mixture of 0,6 g (3,3 mmol) 1,2-diamino-5-cyanonaphthalene and 1,4 g oxalic acid dihydrate in 35 ml 0,5N hydrochloric acid was refluxed for 3 h. After cooling to 25° C., the precipitate was filtered off and washed with water. The crude product was recrystallized (dimethylsulfoxide-methanol) to give 0,35 g (45%) 2,3-dihydroxy-7-cyano-benzo[f]quinoxaline, m.p. >300° C. IR (KBr): 2190 cm$^{-1}$ (nitrile function).

EXAMPLE 22 a. 1-Amino-2-(4-chlorophenylazo)-naphthalene-5-sulphonamide

A solution of 5,75 g (45,1 mmol) 4-chloroaniline in a mixture of 10 ml concentrated hydrochloric acid and 50 ml water was ice-cooled, and then diazotized with 3,17 g (45,1 mmol) sodium nitrite in 50 ml water. 10,0 g (45,0 mmol) 5-aminonaphthalene-1-sulphonamide was dissolved in a warm mixture of 200 ml 4N sulfuric acid, 300 ml acetic acid and 200 ml water. The solution was cooled to ca. 50° C., and then the diazonium salt solution was added. Stirring was continued for a few minutes, and then a solution of 180 g sodium acetate in 600 ml water was added. The pH was adjusted to ca. 5 by addition of 10N sodium hydroxide. The precipitated product was filtered off and washed with water. The crude product was recrystallized from ethanol to give 11,9 g (74%) 1-amino-2-(4-chlorophenylazo)-naphthalene-5-sulphonamide, m.p. 258° C.

b. 1,2-Diamino-naphthalene-5-sulphonamide

To a solution of 18,1 g (SO mmol) stannous chloride dihydrate in 100 ml concentrated hydrochloric acid was added 10,0 g (27,7 mmol) 1-amino-2-(4-chlorophenylazo)-naphthalene-5-sulphonamide. The mixture was stirred at 70° C. for 3 h. After cooling to 25° C., the mixture was poured into 200 ml ice-water. The precipitate was filtered off and washed with 4N hydrochloric acid. The crude product was stirred with ice-water The precipitate was filtered off and washed with ice-water and ethanol to give 6,7 g 1,2-diamino-naphthalene-5-sulphonamide as a hydrochloride salt.

c. 2,3-Dihydroxy-7-sulphamoyl-benzo[f]quinoxaline

A mixture of 5,0 g (21,0 mmol) 1,2-diamino-naphthalene-5-sulphonamide hydrochloride salt and 6,0 g oxalic acid dihydrate in 200 ml 2N hydrochloric acid was refluxed for 2,5 h. After cooling to 25° C., the precipitate was filtered off and washed with water. The crude product was recrystallized (dimethylformamide-water) to give 7,5 g (69%) 2,3-dihydroxy-7-sulphamoyl-benzo[f]quinoxaline, m.p. 420° C. NMR (DMSO-d$_6$): 12,3 (2H, broad s), 8,9 (1H,d), 8,5 (1H,d), 8,2 (1H,d), 7,7 (4H,m).

EXAMPLE 23

2,3-Dihydroxy-6-nitro-7-sulphamoyl-benzo[f]quinoxaline

To a solution of 1,0 g (3,4 mmol) 2,3-dihydroxy-7-sulphamoylbenzo[f]quinoxaline in 25 ml concentrated sulfuric acid was added at 0° C. 0,15 ml 100% nitric acid. Stirring was continued at 0° C. for 30 min, and then the mixture was poured into 100 ml ice-water to give a precipitate. The crude product was recrystallized (dimethylformamide-water) to give 0,7 g (61%) 2,3-dihydroxy-6-nitro-7-sulphamoyl-benzo[f]quinoxaline, m.p. 360° C. NMR (DMSO-d$_6$): 12,4 (1H, broad s), 12,3 (1H, broad s), 8.7 (1H, d), 8.5 (1H,d), 8.17 (1H,s), 7.9 (1H,t), 7.4 (2H, broad s).

EXAMPLE 24

6-Amino-2,3-dihydroxy-7-sulphamoyl-benzo[f]quinoxaline

A solution of 0,5 g (1,49 mmol) 2,3-dihydroxy-6-nitro-7-sulphamoyl-benzo[f]quinoxaline in 5 ml dimethylformamide was hydrogenated at atm. pressure by using ca. 1 g Ra-Ni as a catalyst. The filtered reaction mixture was added 5 ml 1N hydrochloric acid, and then evaporated in vacuo. The crude product was recrystallized (dimethylformamide-water) to give 0,2 g (40%) 6-amino-2,3-dihydroxy-7-sulphamoyl-benzo[f]quinoxaline as a hydrochloride salt. MS: (m/e) 306 (M+; 75%). NMR (DMSO-$_6$): 11,8 (2H, broad s), 8.7 (1H,d), 8.2 (1H,d), 7.6 (3H,m), 6.93 (1H,s), 6.1 (2H, broad s).

The pharmaceutical preparations or compositions comprising the compounds of the invention may be administered to humans or animals by oral or parenteral route.

An effective amount of the active compound or a pharmaceutically-acceptable salt thereof may be determined in accordance with the usual factors, such as the nature and severity of the condition and the weight of the mammal requiring treatment Conventional excipients are such pharmaceutically-acceptable organic or inorganic carrier substances suitable for parenteral or enteral application which do not deleteriously react with the active compounds.

Examples of such carriers are water, salt solutions, alcohols, polyethylene glycols, polyhydroxyethoxylated castor oil, gelatine lactose amylose magnesium stearate talc, silicic acid, fatty acid monoglycerides and diglycerides, pentaerythritol fatty acid esters, hydroxymethylcellulose, and polyvinylpyrrolidone.

The pharmaceutical preparations can be sterilized and mixed, if desired, with auxiliary agents, such as lubricants, preservatives, stabilizers, wetting agents, emulsifiers, salt for influencing osmotic pressure, buffers and/or coloring substances and the like, which do not deleteriously react with the active compounds.

Injectable solutions or suspensions, preferably aqueous solutions with the active compound dissolved in polyhydroxylated castor oil, are particularly suitable for parenteral administration.

Ampoules are convenient unit dosage forms.

Tablets, dragees, or capsules containing talc and/or a carrier or binder or the like are particularly suitable for oral administration. The carrier preferably is lactose and/or corn starch and/or potato starch.

A syrup, elixir, or the like can be used in t he cases where a sweetened vehicle can be employed or is desired.

Generally, the compounds of this invention are dispensed in unit dosage form comprising 10-200 mg of active ingredient in or together with a pharmaceutically-acceptable carrier per unit dosage.

The dosage of the compounds according to this invention is 1-500 mg/day, when administered to patients, e.g., humans, as a drug.

A typical tablet which may be prepared by conventional tabletting techniques contains:

| Core: | |
|---|---|
| Active compound (as free compound or salt thereof) | 100 mg |
| Colloidal silicon dioxide (Aerosil ®) | 1.5 mg |
| Cellulose, microcryst. (Avicel ®) | 70 mg |

| -continued | | |
|---|---|---|
| Modified cellulose gum (Ac-Di-Sol ®) | | 7.5 mg |
| Magnesium stearate | | 1 mg |
| Coating: | | |
| HPMC | approx. | 9 mg |
| *Mywacett 9—40 T ® | approx. | 0.9 mg |

*Acylated monoglyceride used as plasticizer for film-coating

The free compounds of the present invention which form alkali metal or alkaline earth metal salts may be employed in such salt form. Such alkali metal or earth alkali metal salts are ordinarily formed by reacting the dihydroxyquinoxaline compound with an equivalent amount or excess of the selected alkali metal or earth alkali metal as the hydroxide, frequently and suitably by admixture in the presence of a neutral solvent, from which the salt may be precipitated or recovered in other conventional manner, e.g., by evaporation. Administration of a compound of the invention is often preferably in the form of a pharmaceutically-acceptable water-soluble alkali metal or earth alkali metal salt thereof, and orally, rectally, or parenterally in the form of a pharmaceutical composition wherein it is present together with a pharmaceutically-acceptable liquid or solid carrier of diluent.

The compounds of the invention, together with a conventional adjuvant, carrier, or diluent, may be placed into the form of pharmaceutical compositions and unit dosages thereof, and in such form may be employed as solids, such as tablets or filled capsules, or liquids, such as solutions, suspensions, emulsions elixirs or capsules filled with the safe, ell for oral use, in the form of suppositories for rectal administration; or in the form of sterile injectable solutions for parenteral (including subcutaneous) use. Such pharmaceutical composition and unit dosage forms thereof may comprise conventional ingredients in conventional proportions, with or without additional active compounds or principles, and such unit dosage forms may contain any suitable effective glutamate antagonistic, amount of the active ingredient commensurate with the intended daily dosage range to be employed. Tablets containing fifty (50) milligrams of active ingredient or, more broadly, ten (10) to two hundred (200) milligrams, per tablet, are accordingly suitable representative unit dosage forms.

Due to their high degree of glutamate antagonistic activity and their low toxicity, together presenting a most favorable therapeutic index, the compounds of the invention may be administered to a subject, e.g., a living animal body, in need of such glutamate antagonist treatment, elimination, alleviation, or amelioration of an indication which is sensitive to a change in the glutamate receptor condition, e.g., epilepsy, psychosis, dementia, convulsion, or muscle rigidity, often preferably in the form of an alkali metal or earth alkali metal salt thereof, concurrently, simultaneously, or together with a pharmaceutically-acceptable carrier or diluent, especially and preferably in the form of a pharmaceutical composition thereof, whether by oral, rectal, or parenteral (including subcutaneous) route, in an effective amount. Suitable dosage ranges are 1-500 milligrams daily, preferably 10-200 milligrams daily, and especially 50-100 milligrams daily, depending as usual upon the exact mode of administration, form in which administered, the indication toward which the administration is directed, the subject involved and the body weight of the subject involved, and the preference and experience of the physician or veterinarian in charge. Such method of treating may be described as the treatment of an indication caused by or related to hyperactivity of the excitatory neurotransmitters, in a subject in need thereof, which comprises the step of administering to the said subject a neurologically-effective amount of a glutamate antagonistic heterocyclic compound of the invention.

In conclusion, from the foregoing, it is apparent that the present invention provides novel neurologically-effective glutamate antagonistic heterocyclic compounds and salts thereof, having advantageous and unpredictable properties, as well as novel pharmaceutical compositions thereof and method of treating therewith, all possessed of the foregoing more specifically-enumerated characteristics and advantages.

It is to be understood that the invention is not to be limited to the exact details of operation, or to the exact compositions, methods, procedures, or embodiments shown and described, as obvious modifications and equivalents will be apparent to one skilled in the art, and the invention is therefore to be limited only by the full scope of the appended claims.

We claim:

1. A heterocyclic compound having the formula I

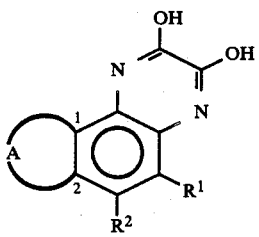

wherein -A- together with the two carbon atoms denoted as 1 and 2 is

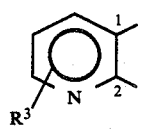

wherein $R^1$, $R^2$ and $R^3$ are independently H, halogen, CN, $NH_2$, $NO_2$, $SO_3H$, $SO_2NH_2$, or $CONH_2$.

2. A pharmaceutical composition comprising as active glutamate antagonistic component an effective amount of a heterocyclic compound having the formula I

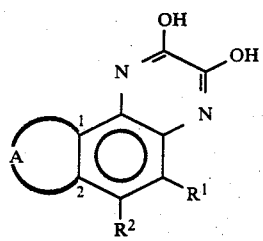

wherein -A- together with the two carbon atoms denoted as 1 and 2 is

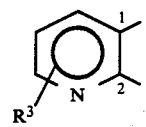

wherein $R^1$, $R^2$ and $R^3$ are independently H, halogen, CN, $NH_2$, $NO_2$, $SO_3H$, $SO_2NH_2$, or $CONH_2$, or a pharmaceutically-acceptable salt thereof, and a pharmaceutically-acceptable carrier.

3. A method of treating hyperactivity of the excitatory neurotransmitters, in a subject in need thereof, which comprises the the step of administering to the said subject a neurologically-effective, glutamate antagonistic, amount of a heterocyclic compound having the formula I

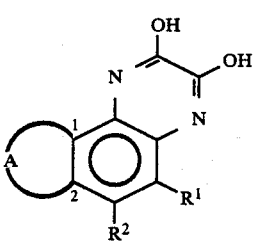

wherein -A- together with the two carbon atoms denoted as 1 and 2 is

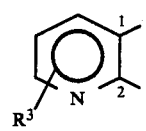

wherein $R^1$, $R^2$ and $R^3$ are independently H, halogen, CN, $NH_2$, $NO_2$, $SO_3H$, $SO_2NH_2$, or $CONH_2$, or a pharmaceutically-acceptable salt thereof.

4. The method of claim 3 wherein the compound is administered in the form of a pharmaceutical composition thereof, in which it is present together with a pharmaceutically-acceptable carrier or diluent.

5. A compound according to claim 1 which is 2,3-dihydroxy-6-nitropyrido (2,3-f) quinoxaline.

6. A pharmaceutical composition of claim 2 wherein the compound is 2,3dihydroxy-6-nitropyrido(2,3-f)quinoxaline.

7. A pharmaceutical composition according to claim 2 in the form of an oral dosage unit containing about 10–200 mg of the active compound.

8. A method of claim 3 wherein the compound is 2,3-dihydroxy-6-nitropyrido(2,3-f)quinoxaline.

* * * * *

UNITED STATES PATENT AND TRADEMARK OFFICE
CERTIFICATE OF CORRECTION

PATENT NO. : 4,912,108                    Page 1 of 3

DATED      : March 27, 1990

INVENTOR(S): Poul Jacobsen, Flemming E. Nielsen and Tage Honore

It is certified that error appears in the above-identified patent and that said Letters Patent is hereby corrected as shown below:

Title Page, [56] References Cited, U.S. PATENT DOCUMENTS; insert before the first reference, the following:
-- 3,431,111   3/1969   Brooker .... 544/343 --

Title Page, [56] References Cited, U.S. PATENT DOCUMENTS; insert after the last reference beginning "4,764,518" the following:
--   OTHER PUBLICATIONS
   Yamatani I, Chem Abs 74, 3658j (1967).
   Yamatani II, Chem Abs 73, 131031r (1967). --

Col. 1, line 27; delete "ps"

Col. 1, line 37; delete "ps"

Col. 3, line 51; "Na30" should read -- Na+ --

Col. 4, line 4; "mino-" should read -- amino- --

Col. 4, line 16; "responces in in vivo" should read -- responses in vivo --

Col. 5, line 15; "is" should read -- are --

Col. 5, line 19; "is" should read -- are --

Col. 5, line 34; delete "cl"

Col. 5, lines 34&35; "$^3$H-AMPA binding (Test 1)" should be a new paragraph and new subheading Col. 5, line 39; "0°0 C." should read -- 0° C. --

Col. 6, line 21; "37°0 C." should read -- 37° C. --

Col. 6, line 44; "relase" should read -- release --

UNITED STATES PATENT AND TRADEMARK OFFICE
CERTIFICATE OF CORRECTION

PATENT NO. : 4,912,108

DATED : March 27, 1990

INVENTOR(S) : Poul Jacobsen, Flemming E. Nielsen and Tage Honore

It is certified that error appears in the above-identified patent and that said Letters Patent is hereby corrected as shown below:

Col. 9, line 53; "hydrochlorid" should read -- hydrochloridic --
Col. 10, line 2; "liqouer" should read -- liquor --
Col. 10, line 20; "powered" should read -- powdered --
Col. 10, line 54; "affored" should read -- afforded --
Col. 11, line 11; "wi" should read -- with --
Col. 11, line 31; delete "?"
Col. 11, line 32; "2H,NH2)" should read -- 2H,NH$_2$) --
Col. 11, line 41; "he" should read -- the --
Col. 11, line 50; "collect ed" should read -- collected --
Col. 11, line 60; "1 2-" should read -- 1,2- --
Col. 12, line 21; "0.B" should read -- 0.8 --
Col. 12, line 29; "J$_{7-91}$" should read -- J$_{7-9}$=1 --
Col. 12, line 45; "triethylaming" should read -- triethylamine --
Col. 13, line 2; "1H-NMR" should read -- $^1$H-NMR --
Col. 13, line 18; "1H-NMR" should read -- $^1$H-NMR --
Col. 13, line 46; "M" should read -- 4M --
Col. 14, line 41; "C.H$_2$" should read -- CH$_2$ --
Col. 14, line 67; "1,2,,4-" should read -- 1,2,3,4- --
Col. 15, line 28; "M+" should read -- M$^+$ --
Col. 16, line 29; "SO" should read -- 80 --
Col. 16, line 37; "ice-water The" should read -- ice-water. The --
Col. 17, line 7; "5 ml" should read -- 75 ml --
Col. 17, line 14; "(DMSO-$_6$)" should read -- (DMSO-d$_6$) --
Col. 17, line 51; "t he" should read -- the --
Col. 18, line 32; "emulsions elixirs" should read -- emulsions, elixirs, --
Col. 18, line 33; "safe, ell" should read -- same, all --

UNITED STATES PATENT AND TRADEMARK OFFICE
CERTIFICATE OF CORRECTION

PATENT NO. : 4,912,108

DATED : March 27, 1990

INVENTOR(S) : Poul Jacobsen, Flemming E. Nielsen and Tage Honore

It is certified that error appears in the above-identified patent and that said Letters Patent is hereby corrected as shown below:

Col. 20, line 27; delete "the" (second occurrence)   (Preliminary

Col. 20, line 61; "2,3dihydroxy-" should read -- 2,3-dihydroxy- --

Signed and Sealed this

Twenty-eighth Day of January, 1992

Attest:

HARRY F. MANBECK, JR.

*Attesting Officer*    *Commissioner of Patents and Trademarks*